(12) United States Patent
Garman (10) Patent No.: US 6,299,445 B1
(45) Date of Patent: Oct. 9, 2001

(54) ENDODONTIC INSTRUMENT, INSTRUMENT BLANK AND METHOD OF MANUFACTURE

(75) Inventor: Gary T. Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/288,173

(22) Filed: Apr. 8, 1999

(51) Int. Cl.[7] .................................................. A61C 3/00
(52) U.S. Cl. ........................................... 433/102; 433/224
(58) Field of Search ................................. 433/81, 102, 224

(56) References Cited

U.S. PATENT DOCUMENTS

| | | | |
|---|---|---|---|
| 4,260,379 | 4/1981 | Groves et al. | 433/102 |
| 5,106,298 | 4/1992 | Heath et al. | 433/102 |
| 5,380,200 | 1/1995 | Heath et al. | 433/102 |
| 5,464,362 | 11/1995 | Heath et al. | 451/48 |
| 5,628,674 | * 5/1997 | Heath et al. | 433/102 X |
| 5,984,679 | * 11/1999 | Farzin-Nia et al. | 433/102 |

OTHER PUBLICATIONS

Kerr Corporation, *New Kerr K–Flex Instrument*, Brochure, 7 pgs., Feb. 1981.
Dr. Edgar Schäfer, *Relationship Between Design Features of Endodontic Instruments and Their Properties, Part 1: Cutting Efficiency*, Article, 22 pgs., undated.
Dr. Edgar Schäfer, *Relationship Between Design Features of Endodontic Instruments and Their Properties, Part 2: Instrumentation of Curved Canals*, Article, 14 pgs., undated.

* cited by examiner

Primary Examiner—Nicholas D. Lucchesi
(74) Attorney, Agent, or Firm—Wood, Herron & Evans, L.L.P.

(57) ABSTRACT

An endodontic instrument including an elongate member having a longitudinal axis, a proximal end, a distal end and a working length between the proximal and distal ends. The working length is formed with a plurality of surface portions cut from the outer surface thereof along paths extending along at least partially around the longitudinal axis. The cut surface portions are then physically twisted to form helical cutting and/or debris removal edges extending around the longitudinal axis. The instrument may be a file or reamer used in root canal procedures and may have three, four or more longitudinally extending surface portions and corresponding edges. The cutting edges define grind angles that vary along the working length. Flexibility of the instrument may also be easily varied according to the invention. Methods of manufacturing the instrument may include grinding flats on the outer surface of a wire blank, with the flats partially twisting around the longitudinal axis. The blank with the partially twisting flats is then physically twisted to form the helical cutting and/or debris removal edges.

28 Claims, 8 Drawing Sheets

FIG. 16

ENDODONTIC INSTRUMENT, INSTRUMENT BLANK AND METHOD OF MANUFACTURE

FIELD OF THE INVENTION

The present invention relates generally to endodontic instruments, such as files and reamers and, more specifically, to those instruments especially useful in root canal procedures.

BACKGROUND OF THE INVENTION

Endodontists use various types of instruments for cleaning and enlarging the root canals of the teeth. In a typical root canal procedure, an endodontist first makes an opening in the surface of the tooth to provide access to the interior. The endodontist then utilizes small instruments, such as hand held files and reamers, to clean and enlarge the narrow, tapered root canals. In a conventional procedure, the endodontist fills the prepared root canals with gutta percha, which is a rubber-like substance, and then seals the tooth with protective cement. The endodontists may sometimes apply a crown to the tooth as a final step.

Typically, the endodontist uses a series of delicate, flexible files to clean out and shape the root canals. Each file includes a proximal and typically including a handle to be gripped between the fingers of the endodontist and a distal end or tip. A working length with helical flutes and cutting edges is located between the proximal and distal ends. The endodontist uses files of increasingly larger diameter to sequentially increase the diameter of the root canal and achieve the desired diameter and shape.

Endodontic root canal files and reamers have been formed from twisted blanks in generally three different configurations. One type is formed by twisting a ground blank having a square cross section to create four helical cutting edges per revolution. Another type consists of a twisted blank of triangular cross section having three cutting edges per revolution. The third type, often referred to as a K-flex type, is formed from a blank having a parallelogram-shaped cross section, such as a rhomboid-shaped cross section. After twisting this type of blank, two cutting edges and two debris removal edges will be formed per revolution. All three of these types of instruments have a tapered major diameter or cross-sectional dimension and a tapered minor diameter or cross-sectional dimension in which the taper angles are generally the same. Also, the angles formed between the surfaces that define the cutting and debris removal edges are constant along the length of the instrument. In other words, a given grind angle of an edge on the instrument remains the same along the entire working length of that instrument.

Existing endodontic files and reamers formed from twisted blanks are designed in such a manner that the minor diameter is purely a function of the major diameter. The undesirable consequences of this type of design become significant for instruments that have a greater taper along the working length. In particular, these instruments become much stiffer toward the proximal end or handle of the instrument. This can cause the instrument to be difficult to maneuver within curved root canals because the instrument may not flex enough to conform to the shape of the canal. Although certain helically fluted endodontic instruments have been formed completely by grinding to achieve more constant flexibility along the length, these instruments have significant drawbacks. First, instruments formed completely by grinding are more costly to manufacture. Also, twisted instruments may be formed in a wide variety of cross-sectional shapes, depending on the shape of a initially ground wire blank.

In view of problems in this field, including those problems noted above, it would be desirable to provide an endodontic instrument, such as a file or reamer formed from a twisted blank, in which the size of one diameter or cross-sectional dimension is formed independent of the other to optimize flexibility, strength and other operating characteristics of the instrument. In this manner, instruments of greater taper may be formed with greater flexibility for maneuvering within curved root canals, while also retaining sufficient strength to resist breakage during use.

SUMMARY OF THE INVENTION

The present invention provides an endodontic instrument, such as a file or reamer or other cutting, shaping or cleaning instrument, comprising an elongate member with optimal flexibility, strength and other operating characteristics. The elongate member includes a longitudinal axis, which is preferably straight when not in use, and a proximal end, a distal end and a working length generally between the proximal and distal ends. The working length is formed with an outer surface comprising a plurality of twisted or curved surface portions defining at least one cutting edge formed at a junction between adjacent surface portions. The adjacent surface portions are preferably both cut from the outer surface along paths extending along and at least partially around the longitudinal axis. There may be only one twisting surface portion or multiple twisting surface portions on a blank ground according to the invention. These cut surface portions are further physically twisted to form helical cutting edges extending around the longitudinal axis.

The adjacent surface portions define a cutting edge or debris removal edge having an angle which, in accordance with one aspect of the invention, varies along the working length. Preferably, the angle defined at each edge decreases in a direction from the distal end to the proximal end. This inventive aspect benefits the instrument in several ways. For example, even at larger tapers, the instrument will be more flexible than conventional instruments of the same taper. Also, one or more cutting edges will be sharper at the proximal end of the working length because of the reduced angle between adjacent surface portions at this location. This allows the proximal end to be a more efficient cutter at that portion of the tooth having the greatest amount of material needing removal. Finally, this inventive aspect also provides an increased area for debris removal at the proximal end.

The invention also enables the minor and major diameters of the instrument to be sized independent of one another. This aspect allows the minor diameter or cross-sectional dimension to be maintained substantially constant along the working length, while the major diameter or cross-sectional dimension includes a taper. Thus, a twisted instrument according to this aspect of the invention will have a more constant flexibility along the working length notwithstanding a significant taper existing along the major diameter. Other embodiments of this general aspect are also possible and include forming the minor and major diameters with different tapers.

Endodontic instruments of this invention may be formed with many different cross sectional shapes. Typically, the elongate member of the finished instrument will have three or four longitudinally extending surface portions and a corresponding number of longitudinal, helically-shaped edges. The elongate member may be formed from materials having superelastic properties and/or other materials, such as titanium, carbon steel or stainless steel.

A preferred method of making endodontic instruments according to the invention includes removing material from an outer surface of a wire blank in at least a first path extending along and twisting at least partially around the longitudinal axis of the wire blank, and then twisting one end of the wire blank with respect to the other and about the longitudinal axis to form at least one helical cutting edge along the working length. Preferably, at least two adjacent surface portions are cut or ground from the outer surface of the wire blank in first and second paths extending along and twisting at least partially around the longitudinal axis of the wire blank. For example, a three-sided endodontic instrument may be formed from a blank ground to have two partially twisting outer surface portions and one straight or axially extending outer surface portion. As another example, a four-sided instrument may be formed with four longitudinally extending, partially twisting ground flats. It will be appreciated that one or more of the ground surface portions may be flats or may have other cross-sectional shapes, such as concave shapes. In the preferred embodiments, the twisting surface portions of the blank will be initially ground such that they twist from about 2° to about 60° about the longitudinal axis along the working length. The working length may be formed in various lengths depending on the intended use of the instrument.

Other features, objects and advantages of the invention will become more readily apparent to those of ordinary skill in the art upon review of the following detailed description of the preferred embodiments, taken in conjunction with the accompanying drawings.

DETAILED DESCRIPTION OF THE PREFERRED EMBODIMENTS

Figure 1:
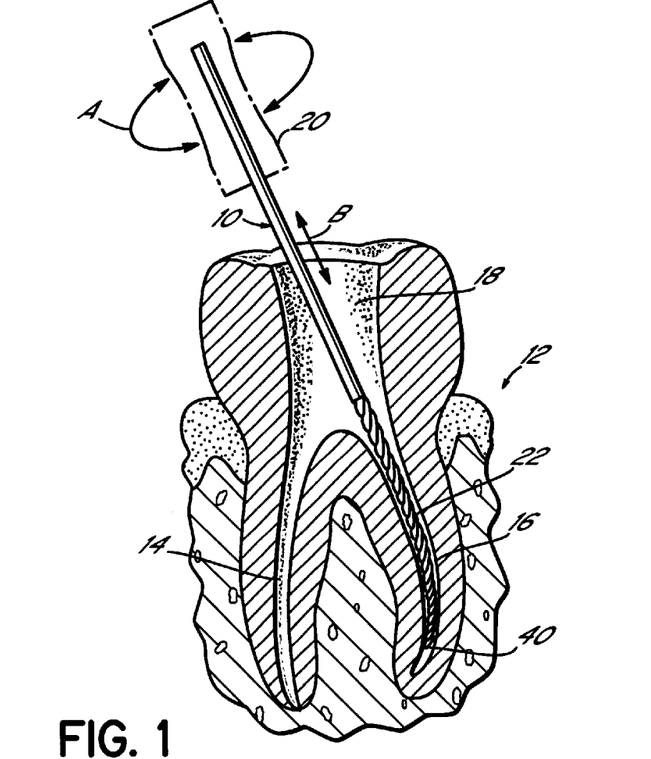
FIG. 1 is a cross sectional view of a tooth and an endodontic instrument in accordance with the invention shown in use within a root canal.

Referring first to FIG. 1, an endodontic instrument 10 constructed in accordance with a preferred embodiment of the invention is shown being used during a root canal procedure on a tooth 12. Tooth 12 includes root canals 14, 16 and an upper interior portion 18 which has been initially opened using another instrument, such as a drill (not shown). Instrument 10 includes a handle 20 for manual gripping by, for example, an endodontist and a working length 22 having helical flutes, as will be discussed in more detail below. Although these instruments are typically manipulated manually, the invention may be adapted to power-operated instruments as well. In a conventional manner, instrument 10 may be rotated in the direction of arrows "A" and reciprocated in the direction of arrow "B" by the endodontist to clean out and enlarge root canal 16.

Figure 2:
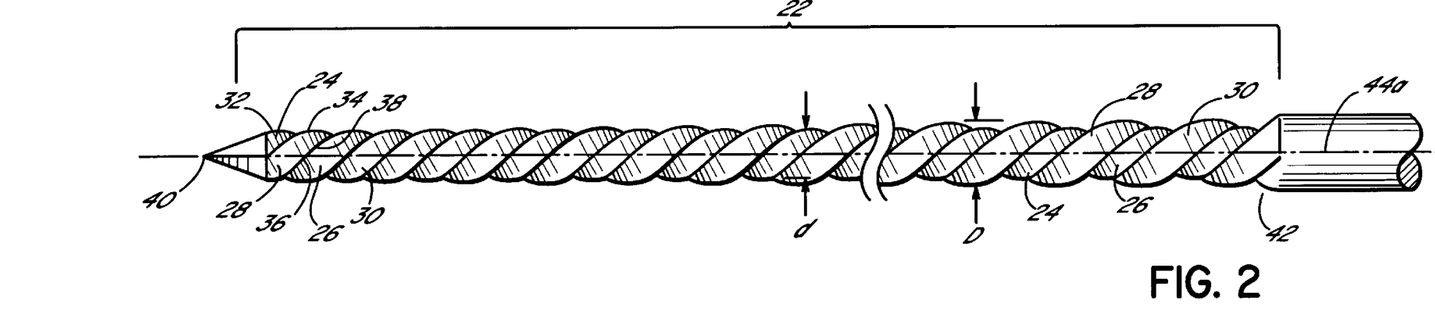
FIG. 2 is an enlarged elevational view of a portion of the endodontic instrument shown in FIG. 1.

As shown in the enlarged view of working length 22 in FIG. 2, respective flutes are formed by twisted surface portions 24, 26, 28, 30. These surface portions 24, 26, 28, 30 are defined between respective edges 32, 34, 36, 38. As further shown in FIG. 2, and explained in more detail below, a minor diameter or cross-sectional dimension "d" and a major diameter or cross-sectional dimension "D" are evident along the working length 22. Minor diameter "d" preferably remains substantially constant along working length 22, while major diameter "D" becomes progressively larger in a direction extending from distal end 40 to proximal end 42 of working length 22. Due to the substantially constant minor diameter "d" extending along the working length 22, the flexibility of working length 22 is maintained generally constant along working length 22. As will also be discussed below, minor diameter "d" may also have a taper so as to increase slightly in diameter from distal end 40 toward proximal end 42. However, the rate of taper is preferably substantially less than the rate of taper of major diameter "D". For example, the rate of taper for minor diameter "d" may be in the range of 0 to about 0.06, while the rate of taper for major diameter "D" may be in the range of about 0.02 to about 0.14.

FIGS. 3A–3F illustrate a preferred method of manufacturing instrument 10. In this regard, a cylindrical wire 44 has distal end to initially ground to a sharp point. Wire 44 may be formed of any suitable material used for endodontic instruments of this type. As a few examples, such materials include superelastic materials such as NiTi, or other materials such as titanium, carbon steel or stainless steel. A grinding wheel 48 is used to sequentially grind four longitudinally extending, partially twisting surface portions along wire 44. Specifically, as shown by the end view of wire 44 in FIGS. 3A and 3B, grinding wheel 48 is rotated as wire 44 translates with respect thereto along its center axis 44a. Simultaneously, wire 44 is rotated through an angle α of, preferably, between about 2° and about 60°. This forms surface portion 30.

Figure 3A:
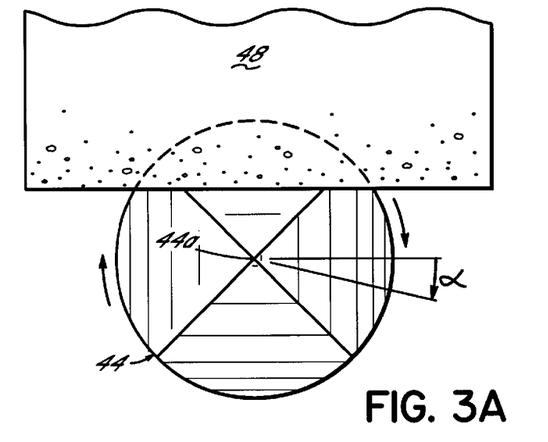
FIG. 3A is an end view of an initial step in a grinding process used to form the endodontic instrument of FIGS. 1 and 2.
Figure 3B:
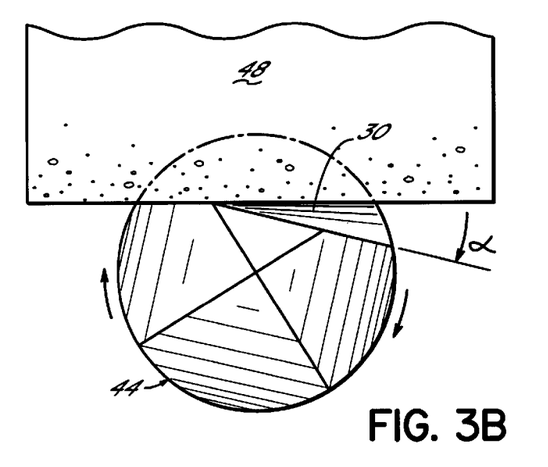
FIG. 3B is a view similar to FIG. 3A, but showing the wire blank rotated during the grinding process.

In the preferred embodiment, for example, wire 44 may be ground along a working length of about 4 mm to about 23 mm. Wire 44 is translated along grinding wheel 48 at a rate of about 100 in./min depending on the material and the size of wire 44. Simultaneously, wire 44 is rotated clockwise about its center axis 44a preferably at a constant rate through an angle of about 2–60° until a position is reached as shown in FIG. 3B and, in solid lines, in FIG. 3F at the proximal end of the working length. During each of the grinding operations, as wire 44 translates past grinding wheel 48, grinding wheel 48 is moved away from the center axis 44a of wire 44 at a preferred rate of about 0.5 in./min. depending on the wire translation rate mentioned above and the desired taper. This rate may change for the different surface portions. The depth of cut may be about 0.005 inches depending on the instrument size and material and the initial wire diameter is preferably 0.041 inches.

Figure 3C:
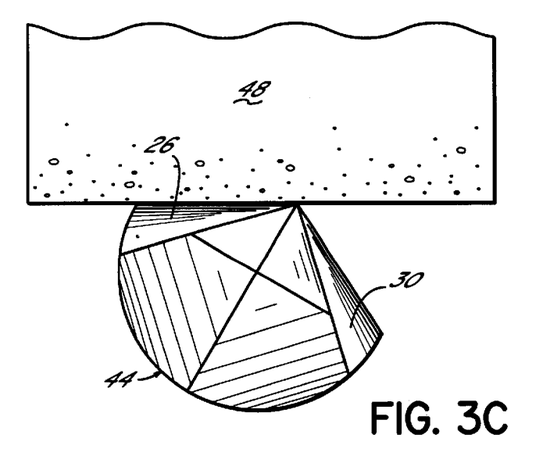
FIG. 3C is a view similar to FIGS. 3A and 3B, but showing the grinding process of a second surface portion.
Figure 3D:
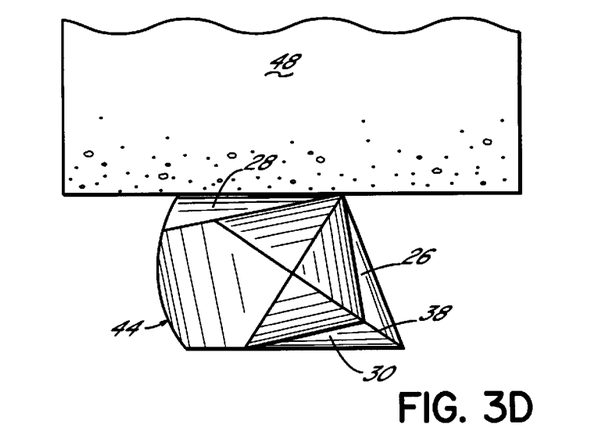
FIG. 3D is a view similar to FIGS. 3A–3C, but showing a grinding process for a third surface portion.
Figure 3E:
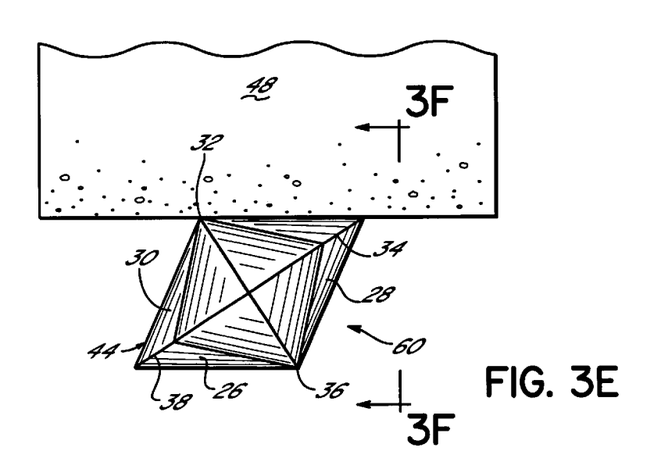
FIG. 3E is a view similar to FIGS. 3A–3D, but showing the grinding process for a fourth surface portion.
Figure 3F:
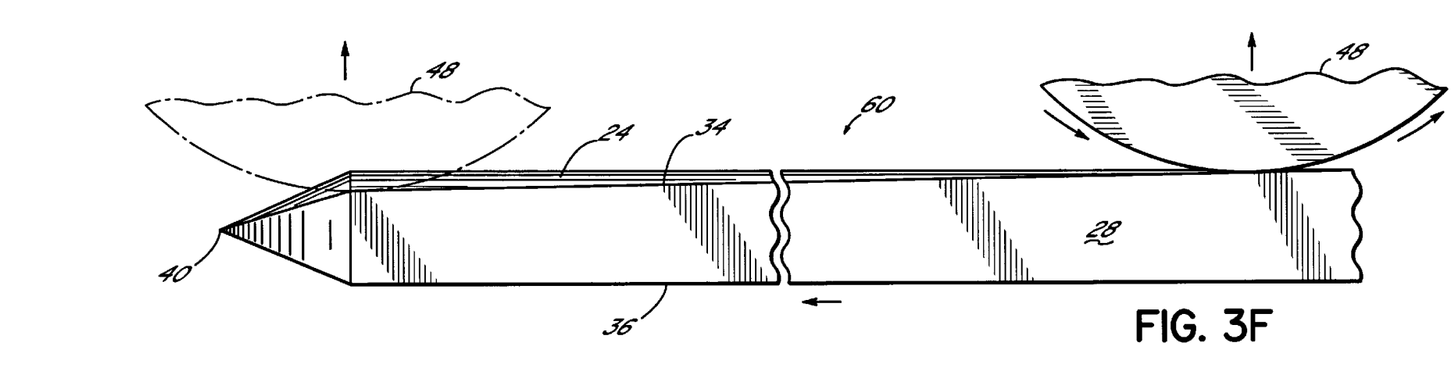
FIG. 3F is a side elevational view taken along line 3F—3F of FIG. 3E.
Figure 4:
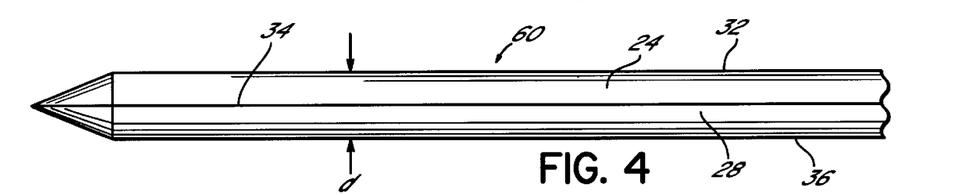
FIG. 4 is a fragmented side elevational view showing the minor diameter of a blank ground in accordance with FIGS. 3A–3E.
Figure 5:
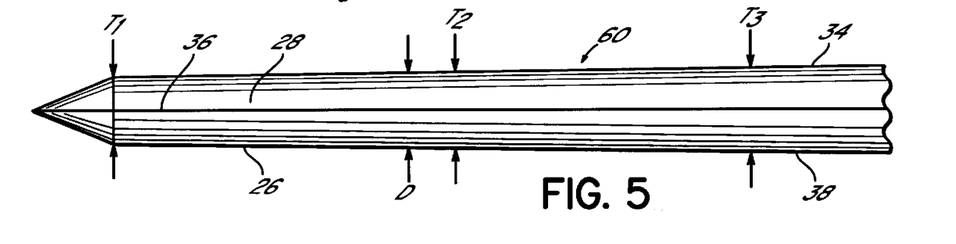
FIG. 5 is a fragmented side elevational view showing the major diameter of the blank shown in FIG. 4.
Figure 6:
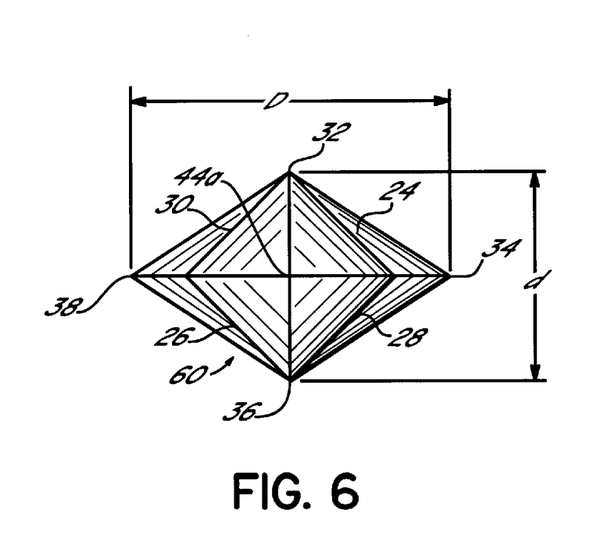
FIG. 6 is an end view of the blank ground in accordance with FIGS. 3A–3E.

To form a four-sided configuration, wire 44 is indexed by 90° and the identical procedure is used to form another surface portion 26 as shown in FIG. 3C. As shown in FIG. 3C, however, wire 44 is rotated counterclockwise during grinding. As shown in FIG. 3D, a third surface portion 28 is formed after another 90° index and, as shown in FIG. 3E, a fourth surface portion 26 is identically formed after a final 90° indexing operation. In the above-described manner, a ground blank 60 as shown in FIGS. 4, 5 and 6, is constructed and ready to be physically twisted by any conventional method into a final instrument 10 as shown in FIG. 2. One suitable twisting method is disclosed in U.S. patent application Ser. No. 09/014,139, assigned to the assignee of the present invention and the disclosure of which is hereby fully incorporated by reference.

Figure 7:
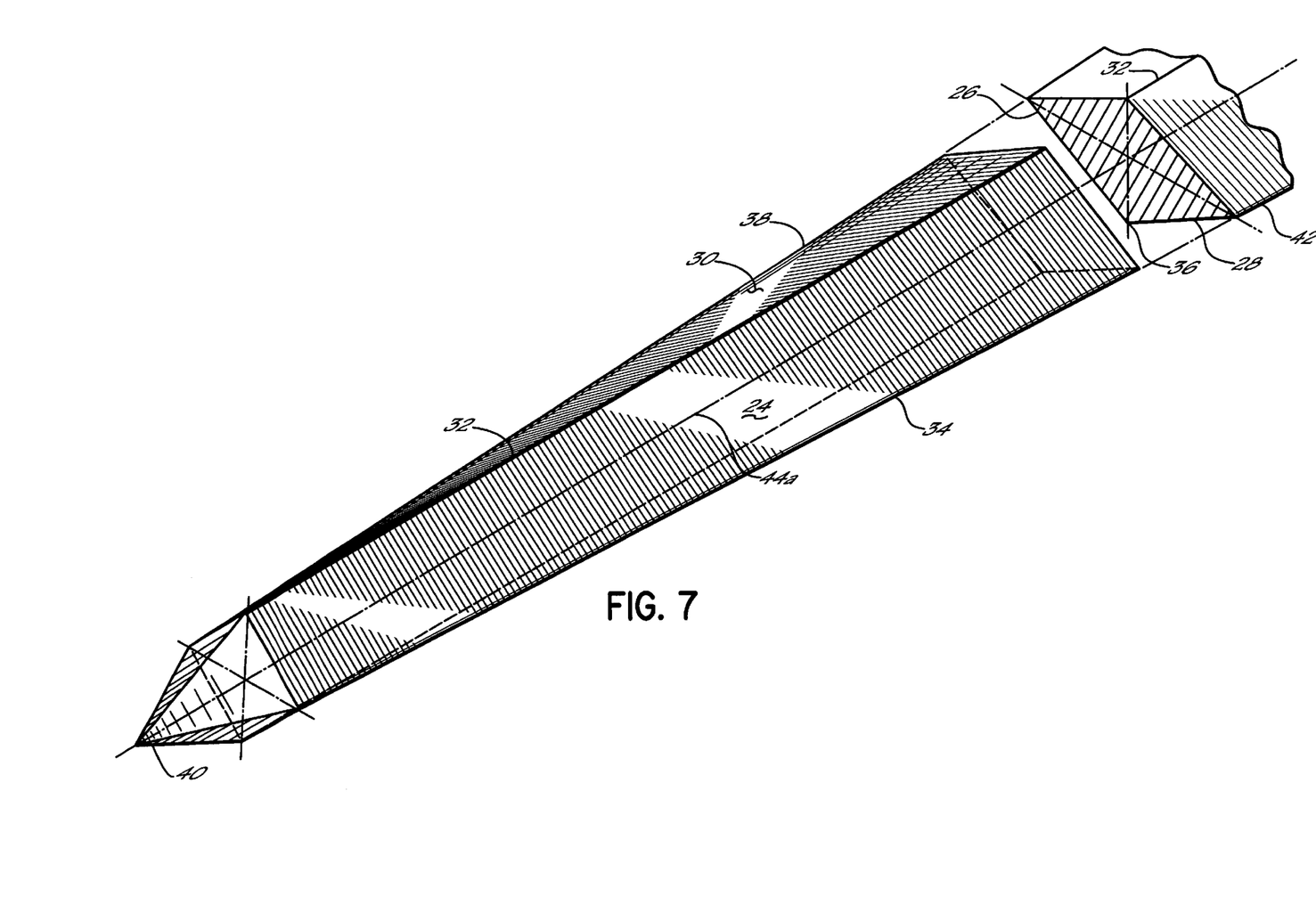
FIG. 7 is a perspective view of the blank ground in accordance with FIGS. 3A–3E.

As further shown in FIGS. 4, 5 and 6, ground blank 60 will have a minor diameter "d", as shown in FIG. 4, which may be substantially constant or slightly tapered along working length 22. A major diameter "D", as shown in FIG. 5, tapers more significantly as shown by dimensions T1, T2, T3. As further shown in FIG. 7, each surface portion 24, 26, 28, 30 gradually widens from about distal end 40 toward proximal end 42 and partially twists about axis 44a of ground blank 60. The cross section of ground blank 60, in this embodiment, transforms from a relatively square cross section proximate distal end 40 to a rhomboid cross section at proximal end 42. As further evidenced in FIG. 6, edges 34, 38 will be sharper at proximal end 42 than at distal end 40. Distal end 40 may be of rhomboid cross section, however, the rhomboidal shape at distal end 40 will not be as exaggerated as at proximal end 42. Once ground blank 60 have been formed, it may be twisted in any conventional manner, such as in the manner disclosed in U.S. patent application Ser. No. 09/014,139, assigned to the assignee of the present invention and the disclosure of which is hereby fully incorporated by reference.

Figure 8A:
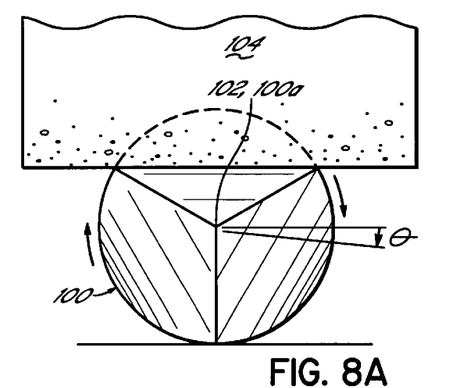
FIG. 8A is an end view of an initial step in a grinding process used to form a blank for a three-sided endodontic instrument constructed in accordance with the invention.
Figure 8B:
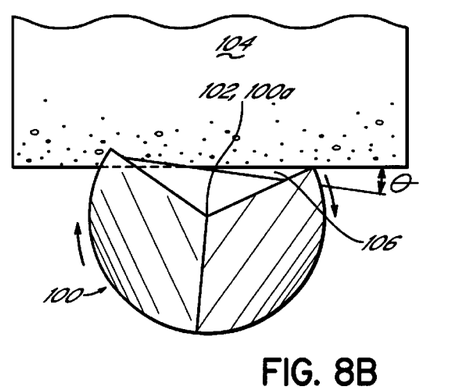
FIG. 8B is a view similar to FIG. 8A, but showing the blank rotated during the grinding process.

FIGS. 8A–8D illustrate the grinding process used for an illustrative three-sided instrument manufactured according to the invention. Specifically, as shown in FIGS. 8A and 8B, a wire 100 has already been ground proximate a distal end 102 so as to form a sharp point. The wire is otherwise preferably cylindrical. Wire 100 is then positioned adjacent a grinding wheel 104 in a manner similar to the first embodiment. Grinding wheel 104 is used to sequentially grind three longitudinally extending surface portions 106, 108, 110. In this embodiment, only surfaces 106 and 108 are ground to be partially twisting surface portions as described above with respect to the first embodiment. Surface portion 110 is a straight, tapered surface portion which does not twist about central axis 100a of wire 100. More specifically, as shown by the end view of wire 100 in FIGS. 8A and 8B, grinding wheel 104 is rotated as wire 100 translates with respect thereto along center axis 100a. Simultaneously, wire 100 is rotated through an angle θ of, preferably, between about 2° and about 60°. The other parameters, such as working length dimension, translation rate, and rotation rate of wire 100 may be as described above with respect to the first embodiment. The rate at which grinding wheel 104 is moved away from center axis 100a and the depth of cut may also be generally the same as described with respect to the first embodiment.

Figure 8C:
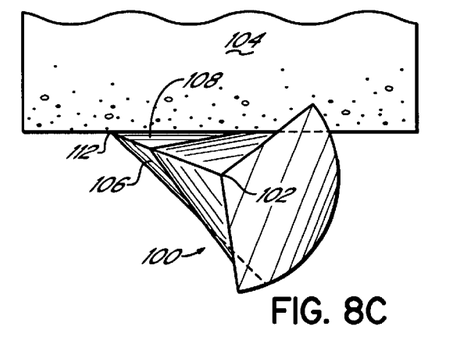
FIG. 8C is a view similar to FIGS. 8A and 8B, but showing the grinding process of a second, partially twisting surface portion.

To form second surface portion 108, wire 100 is indexed by 120° and the identical procedures are used to grind surface portion 108 as shown in FIG. 8C. As shown in FIG. 8C, wire 102 is rotated counterclockwise instead of clockwise during the grinding process. This forms cutting edge 112 defined between surface portions 106 and 108, with cutting edge 112 preferably having the same general characteristics as cutting edges 34, 38 formed in the first embodiment.

Figure 8D:
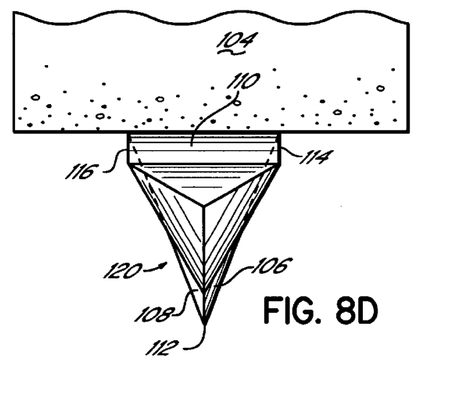
FIG. 8D is a view similar to FIGS. 8A–8C, but showing a grinding process for a third, straight surface portion.
Figures 9, 11:
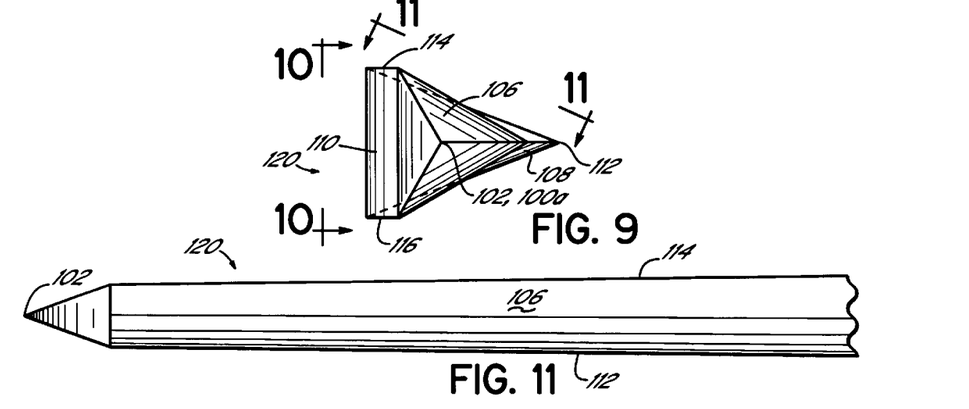
FIG. 9 is an end view of the three-sided blank ground in accordance with the invention.
FIG. 11 is a fragmented side elevational view taken along line 11—11 of FIG. 10 and showing the major diameter of the blank.
Figure 10:
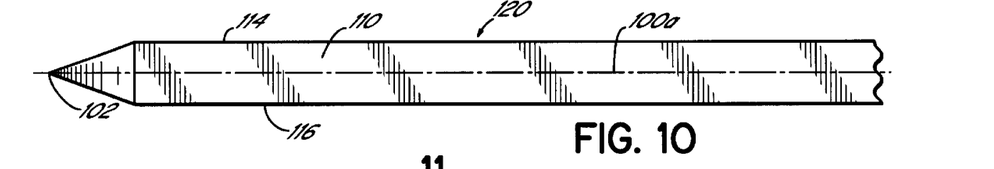
FIG. 10 is a fragmented side elevational view taken along line 10—10 of FIG. 9 and showing the minor diameter of the blank.

As shown in FIG. 8D, third surface portion 110 is formed after another 120° indexing step. This surface portion 110, however, is not a twisted surface portion and therefore wire 100 is not rotated as surface portion 110 is ground by wheel 104. Instead, wire 100 is translated axially with respect to grinding wheel 104 as grinding wheel 104 is moved away from center axis 100a to create a desired taper away from distal end 102. This final grinding operation therefore creates two debris removing edges 114, 116 respectively defined between surface portions 106, 110 and 108, 110.

Figure 12:
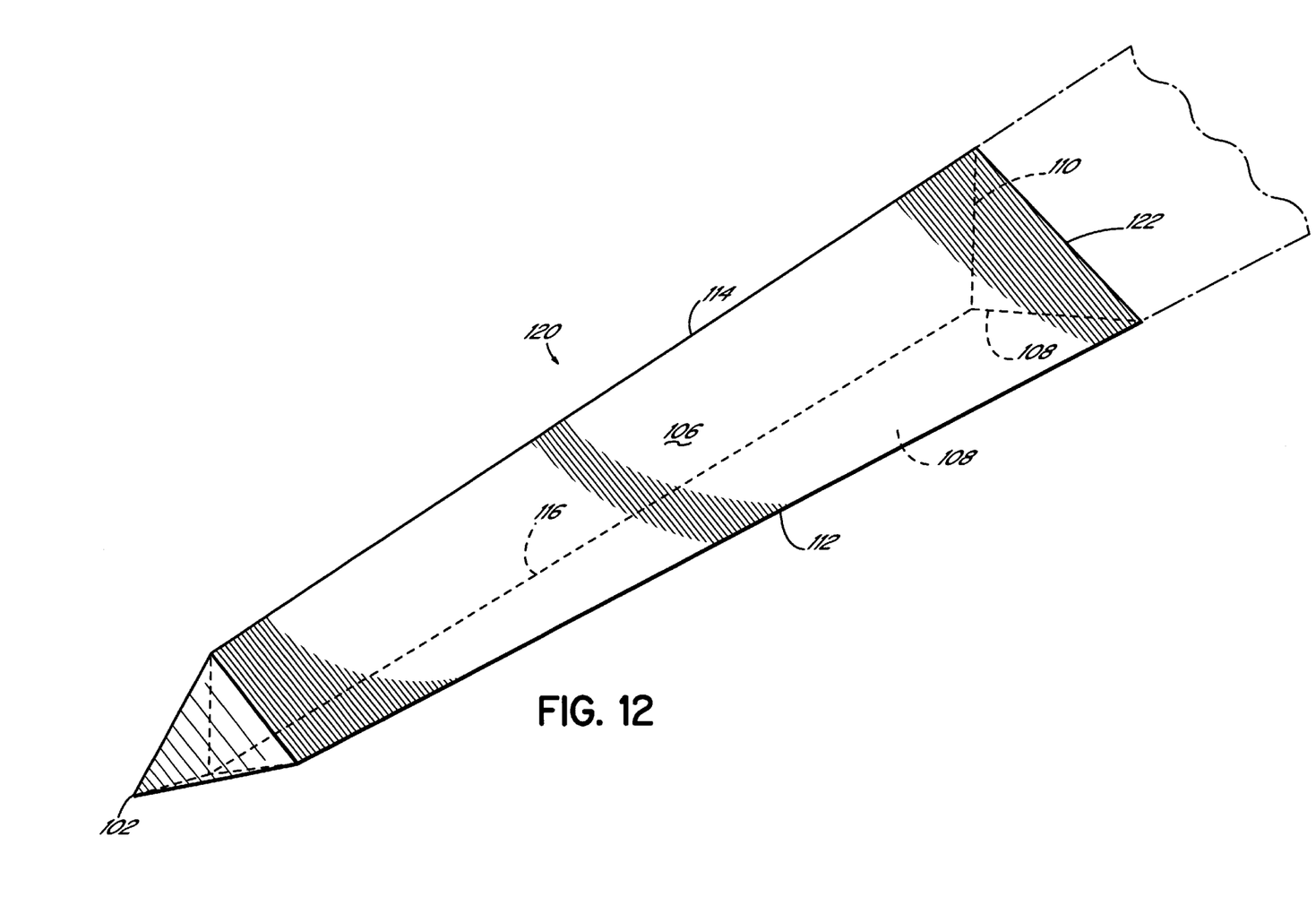
FIG. 12 is a perspective view of the three-sided blank ground in accordance with FIGS. 8A–8D.
Figure 13:
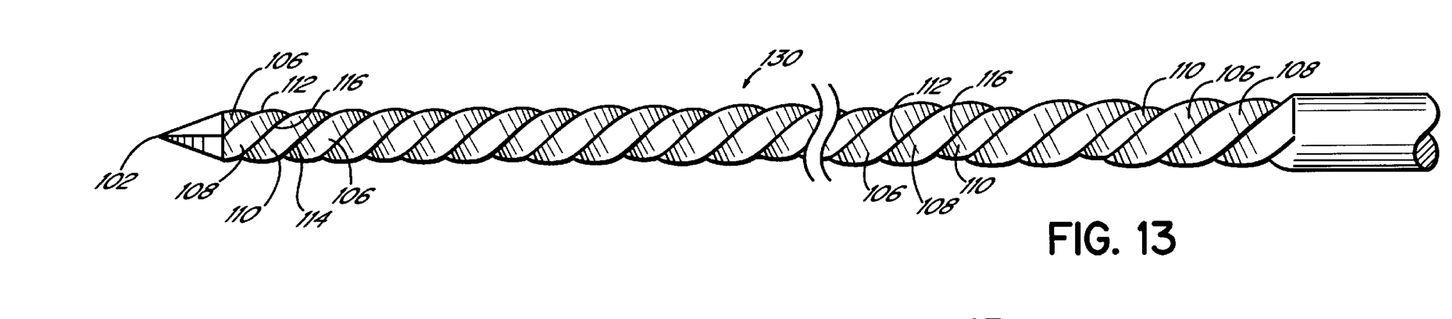
FIG. 13 is a fragmented, elevational view of a twisted instrument formed from the three-sided blank of FIG. 12.

The resulting ground blank 120 is best illustrated in FIGS. 9–12. As will be best appreciated from a review of FIGS. 9 and 12, cutting edge 112 will become sharper moving in a direction from distal end 102 toward a more proximal portion 122 (FIG. 12). The triangular cross-sectional shape of ground blank 120 will also change from more of an equilateral triangular shape adjacent distal end 102 to a more isosceles triangle toward proximal portion 122. Blank 120 is preferably twisted using conventional methods into an instrument 130 as, for example, shown in FIG. 13. Due to the relatively large angle between respective surface portions 106, 110 and 108, 110, edges 114, 116 will function more to remove debris than to cut tissue during, for example, a root canal procedure as generally illustrated in FIG. 1. It will be appreciated that the embodiment of this invention shown in FIGS. 8–12 is only one alternative embodiment and that many additional alternatives are possible. These alternatives may, for example, include three-sided ground blanks with each of the three surface portions at least partially twisting about the axis of the blank or other multi-sided ground blanks which are subsequently physically twisted and which include at least one surface portion which has been ground to at least partially twist about the axis of the blank.

Figure 14:
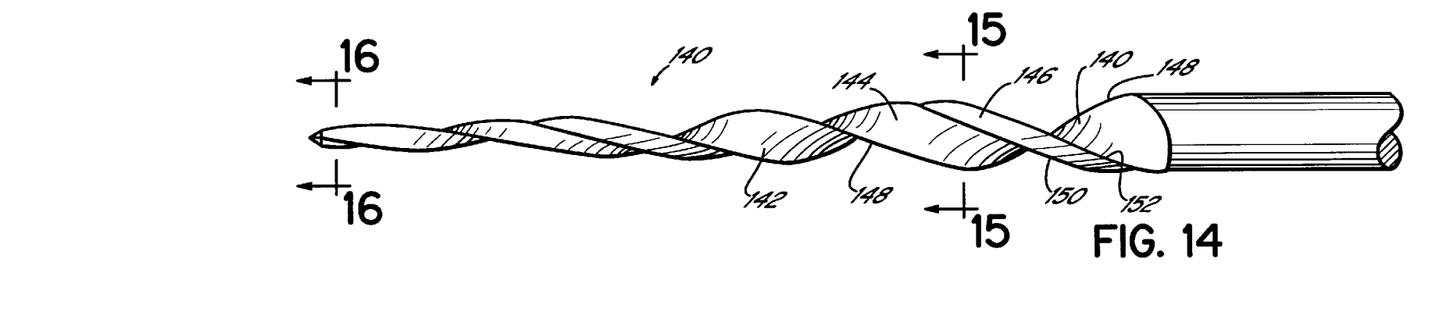
FIG. 14 is a fragmented, elevational view of an alternative endodontic instrument twisted from a three-sided blank.
Figure 15:
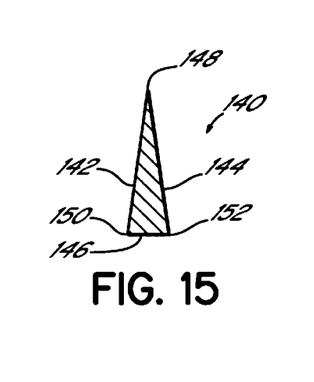
FIG. 15 is a cross-sectional view taken along line 15—15 of FIG. 14.
Figure 16:
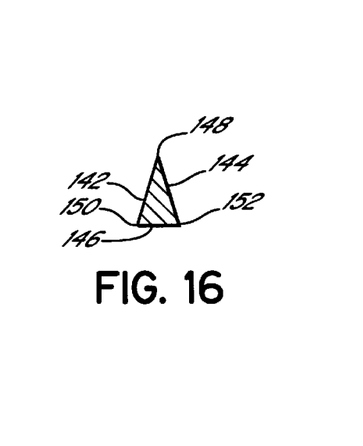
FIG. 16 is a cross sectional view taken along lines 16—16 of FIG. 14.

FIGS. 14–16 illustrate one possible alternative embodiment of a twisted instrument 140 constructed from a three-sided blank which may be formed by the method shown and described in connection with FIGS. 8A–8D. More specifically, instrument 140 includes two surfaces 142, 144 which are ground with at least a partial twist and a third surface 146 having a straight, tapered grind. The differences between this embodiment and the previous embodiment essentially involve physical characteristics of the three-sided blank. For example, it will be noted that the taper along the length of instrument 140 is more exaggerated in the embodiment of FIG. 14 as compared to FIG. 13. Also, the number of twists is less in the embodiment of FIG. 14. Although more exaggerated, it will again be appreciated that instrument 140 has a cross sectional shape at the distal end (FIG. 16) which is closer to an equilateral triangle than at the proximal end (FIG. 15), which is a more elongated triangular shape. Instrument 140 may have a different number of twists than the number shown in FIG. 14. Like the second embodiment, instrument 140 includes a cutting edge 148 defined between surfaces 142, 144. The remaining two edges 150, 152 will essentially function as debris removal edges.

While the present invention has been illustrated by a description of the preferred embodiment and while this embodiment has been described in some detail, it is not the intention of the Applicant to restrict or in any way limit the scope of the appended claims to such detail. Additional advantages and modifications will readily appear to those skilled in the art. This has been a description of the present invention, along with the preferred methods of practicing the present invention as currently known. However, the invention itself should only be defined by the appended claims, wherein

I claim:

1. A method of making an endodontic instrument from a wire blank having an outer surface, a longitudinal axis, and a working length disposed generally between proximal and distal ends, the method comprising:

removing material from the outer surface of the wire blank in at least a first path extending along and twisting at least partially around the longitudinal axis, and twisting at least one of the proximal and distal ends with respect to the other and about the longitudinal axis to form at least one helical cutting edge along the working length.

2. The method of claim 1 further comprising:

prior to twisting the wire blank, removing material from the outer surface of the wire blank in at least a second path extending along and twisting at least partially around the longitudinal axis of said wire blank.

3. The method of claim 2, further comprising:

prior to twisting the wire blank, removing material from the outer surface of the wire blank in at least a third path extending along the working length.

4. The method of claim 3, wherein the third path twists at least partially around the longitudinal axis of said wire blank.

5. The method of claim 4, further comprising:

prior to twisting the wire blank, removing material from the outer surface of the wire blank in at least a fourth path extending along and twisting at least partially around the longitudinal axis of said wire blank.

6. The method of claim 1, wherein the step of removing material further comprises:

grinding a flat surface portion on the outer surface and along said first path.

7. An endodontic instrument comprising:

an elongate member including a longitudinal axis, a proximal end, a distal end and a working length with an outer surface generally located between the proximal and distal ends, and a plurality of lengthwise extending surface portions ground from the outer surface with at least one of said surface portions ground to extend along and at least partially around the longitudinal axis, and said cut surface portions further twisted to form at least one helical cutting edge extending around said longitudinal axis.

8. The endodontic instrument of claim 7, wherein at least two of said surface portions are ground to extend at least partially around said longitudinal axis.

9. The endodontic instrument of claim 7, wherein at least three of said surface portions are ground to extend at least partially around said longitudinal axis.

10. The endodontic instrument of claim 7, wherein at least four of said surface portions are ground to extend at least partially around said longitudinal axis.

11. The endodontic instrument of claim 7, wherein the elongate member is formed from a superelastic material.

12. The endodontic instrument of claim 11, wherein the superelastic material includes nickel-titanium.

13. The endodontic instrument of claim 7, wherein the elongate member is formed from a material including steel.

14. An endodontic instrument comprising:

an elongate member including a longitudinal axis, a proximal end; a distal end and a working length with an outer surface located generally between the proximal and distal ends, a plurality of helically twisting, lengthwise extending surface portions on the outer surface of said working length, and a first helical cutting edge formed at a junction between adjacent surface portions, said first helical cutting edge defined by an angle between said adjacent surface portions which varies along the working length.

15. The endodontic instrument of claim 14, wherein said angle decreases in a direction from said distal end toward said proximal end.

16. The endodontic instrument of claim 15 further comprising three of said helically twisting, lengthwise extending surface portions forming said first helical cutting edge and further forming a second helical cutting edge also defined by an angle between two of said three surface portions which varies along the working length.

17. The endodontic instrument of claim 16 further comprising four of said helically twisting, lengthwise extending surface portions.

18. The endodontic instrument of claim 14 further comprising three of said helically twisting, lengthwise extending surface portions forming said first helical cutting edge and further forming a second helical cutting edge also defined by an angle between two of said three surface portions which varies along the working length.

19. The endodontic instrument of claim 18 further comprising four of said helically twisting, lengthwise extending surface portions.

20. The endodontic instrument of claim 14, wherein the elongate member is formed from a superelastic material.

21. The endodontic instrument of claim 20, wherein the superelastic material includes nickel-titanium.

22. The endodontic instrument of claim 14, wherein the elongate member is formed from a material including steel.

23. A blank used in the formation of an endodontic instrument, the blank comprising an elongate member including a longitudinal axis and having a proximal end, a distal end and a working length with an outer surface located generally between the proximal and distal ends, said working length formed from a plurality of surface portions ground lengthwise from the outer surface, wherein at least one of said surface portions is ground along a path extending along and at least partially around the longitudinal axis.

24. The blank of claim 23, wherein at least two of said surface portions are ground along paths extending along and at least partially around the longitudinal axis.

25. The blank of claim 23, wherein three of said surface portions are ground along paths extending along and at least partially around the longitudinal axis.

26. The blank of claim 23, wherein at least four of said surface portions are ground along paths extending along and at least partially around the longitudinal axis.

27. The blank of claim 23, wherein said one surface portion becomes progressively wider in a direction extending from said distal end to said proximal end.

28. The blank of claim 23, wherein said one surface portion and an adjacent surface portion converge at an angle and said angle becomes progressively smaller in a direction extending from said distal end toward said proximal end.

\* \* \* \* \*